(12) United States Patent
Lahanas et al.

(10) Patent No.: US 6,306,384 B1
(45) Date of Patent: Oct. 23, 2001

(54) SKIN BATTERY COSMETIC COMPOSITION

(75) Inventors: Konstantinos M. Lahanas, Paramus, NJ (US); Daniela Toma, Floral Park, NY (US); Joseph Gubernick, New York, NY (US); Gheorghe Cioca, Lake Grove, NY (US)

(73) Assignee: E-L Management Corp., New York, NY (US)

( * ) Notice: Subject to any disclaimer, the term of this patent is extended or adjusted under 35 U.S.C. 154(b) by 0 days.

(21) Appl. No.: 08/724,455

(22) Filed: Oct. 1, 1996

(51) Int. Cl.$^7$ .................. A61K 31/74; A61K 33/26; A61K 33/24
(52) U.S. Cl. .................. 424/78.1; 424/648; 424/649
(58) Field of Search .................. 424/78.1, 78.02, 424/648, 649; 604/20; 607/75

(56) References Cited

U.S. PATENT DOCUMENTS

| | | | | |
|---|---|---|---|---|
| 4,164,226 | * | 8/1979 | Tapper | 607/75 |
| 5,160,316 | * | 11/1992 | Henley | 604/20 |
| 5,215,520 | * | 6/1993 | Shroot et al. | 604/20 |
| 5,443,441 | * | 8/1995 | De Clauiere | 604/20 |
| 5,503,632 | * | 4/1996 | Haak | 604/20 |
| 5,533,971 | * | 7/1996 | Phipps | 604/20 |

OTHER PUBLICATIONS

Robert Edelberg, Ph.D., The Biophysical Properties of the Skin, Chapter 15, Wiley Interscience, 1971.
Barker et al., Am. J. Physiological Society, The Glabrous Epidermis of Cavies Contains a Powerful Battery.
Carley, et al., Electrotherapy for Acceleration of Wound Healing: Low Intensity Direct Current, Phys. Med. Rehabil., pp. 443–446, 1985.
Accel. Healing of Ischemic Skin Ulcers By Computer–Assisted Low Level Electrostimulation And The Intracellular Physiological Mechanisms Involved, Pub. of Instit. of Bio–Molecular Ed. & Res., 1987.

* cited by examiner

Primary Examiner—Thurman K. Page
Assistant Examiner—Blessing Fubara
(74) Attorney, Agent, or Firm—Karen A. Lowney, Esq.

(57) ABSTRACT

The present invention relates to a method for preventing or treating skin damage which comprises applying to the skin a composition containing an effective amount of a cosmetically or pharmaceutically acceptable compound capable of acting as an electron donor, simultaneously or substantially simultaneously with the application of a composition containing an effective amount of a cosmetically or pharmaceutically acceptable compound capable of acting as an electron acceptor, whereby an exchange of electrons between the electron donor and electron acceptor results in generation of an electrical current on the skin.

24 Claims, No Drawings

SKIN BATTERY COSMETIC COMPOSITION

FIELD OF THE INVENTION

The present invention relates to a novel cosmetic composition and treatment. More specifically, the invention relates to a skin treatment which provides a beneficial mild electrical current across the skin, whereby skin quality is improved.

BACKGROUND OF THE INVENTION

It has long been recognized that there is a normal transcutaneous electric potential associated with mammalian skin (see, e.g., Robert Edelberg, in, The Biophysical Properties of the Skin, Harry Elden(ed.), Chapter 15, Wiley Interscience, 1971). This potential is to a great extent influenced by the presence of sweat glands and hair, and thus the strength of the potential may differ both spatially and temporally on the skin. However, even in nonglandular areas of the skin, there is a fairly strong, measurable current produced across the epidermis, in essence a skin battery. Although most measurements have been conducted on non-human mammals, considerable evidence exists for the same type of battery to exist on human skin as well(Barker et al., Am. J. Physiol. 242: R358-R366, 1982). Such batteries have been known to exist in amphibians, where they apparently serve a function in sodium uptake and appendage regeneration. However, their purpose in a nonaquatic vertebrate was not readily apparent. Based on observations of fairly strong voltage gradients at the margins of wounds, Barker et al. and others have suggested that in mammals the skin currents may be important in the process of wound healing.

Further evidence of the importance of electrical currents in the maintenance of healthy skin has been shown in the successful use of electrotherapy in treatment of skin ulcers. For example, Carley and Wainapel(Arch. Phys. Med. Rehabil. 66: 443–446, 1985 have shown that treatment of indolent ulcers with low density direct current significantly increased the healing rate of those treated individuals relative to individuals treated with conventional therapy, with a concomitant reduction in pain and discomfort in those treated with electrotherapy. Similarly, Biedebach, noting the "wound current" generated in damaged tissue in and also summarizing the overwhelming evidence of the healing properties of electrotherapy for ulcer treatment, proposed that enhancement of the natural current may be useful in accelerating the healing process.

There appears to be no doubt that the maintenance of an electric current on the skin is associated with the continued well-being of undamaged skin, and that application of a current to injured skin can be highly beneficial to the healing process of damaged skin. In addition to the reported treatment of ulcers, there are a number of other skin conditions involving irritation or inflammation which could also potentially benefit from preventive and/or therapeutic application of a low intensity current. However, the means for delivery of healing current to skin reported in the medical literature typically involve the use of machinery and monitoring which would be prohibitively expensive and complicated for the treatment of less serious skin disorders. It therefore would be desirable to have available a less intrusive, more cost-effective method of current delivery to the skin, which method could then benefit less life-threatening, but nonetheless painful and irritating, chronic and acute skin conditions, or simply to maintain the overall health of the skin. The present invention provides just such a method, which can be used routinely by the afflicted individual in an unmonitored home environment.

SUMMARY OF THE INVENTION

The present invention relates to a method for preventing or treating skin damage which comprises applying to the skin an effective amount of a cosmetically or pharmaceutically acceptable compound capable of acting as an electron donor, simultaneously or substantially simultaneously with the application of a cosmetically or pharmaceutically acceptable compound capable of acting as an electron acceptor, whereby an exchange of electrons between the electron donor and electron acceptor results in generation of an electrical current on the skin. The invention also provides a unit package comprising, in separate containers or compartments, a cosmetically or pharmaceutically acceptable carrier comprising a compound capable of acting as an electron donor, and a cosmetically or pharmaceutically acceptable carrier comprising a compound capable of acting as an electron acceptor. In a preferred embodiment, the carrier is one which is capable of facilitating the transfer of electrons between the electron donor and acceptor.

DETAILED DESCRIPTION OF THE INVENTION

Application of the composition(s) of the invention in the present method essentially creates a battery on the skin. A standard battery, outside the present context, is defined as one or more electronically connected electrochemical cells having terminal contacts to produce electrical energy. Briefly, in all battery systems, an oxidizer, or electron acceptor, and fuel, or electron donor, react to form products resulting in direct electron transfer and release or absorption of energy or the performance of work. Most batteries are porous structures in which an interconnected matrix of solid particles, consisting of both non-conductive and conductive materials, is filled with an electrolyte. The electrolyte acts as a conduit in the transfer of electrons.

The present method and compositions operate on the skin in much the same way as a standard battery does in a car or in a portable radio. Like a traditional battery, one component of the two part composition acts as a negative electrode that releases electrons into an external circuit; a second component acts as a positive electrode that gains electrons from an external circuit. Each component is maintained in a matrix which is capable of acting as an electrolyte, i.e., to facilitate the electron transfer between anode and cathode.

Like a traditional battery, the active materials in the two components are selected for their ability to respectively, either donate or accept electrons. In the present method and compositions, the active materials must of course be chosen from among cosmetically or pharmaceutically acceptable materials. However, given this guideline, the first electrode is usually a metallic element, or an oxide or salt thereof, with a positive oxidation potential, i.e., capable of giving up electrons. Examples of such metallic elements include, but are not limited to, copper or iron. The second electrode is often a metal oxide, hydroxide, halide or sulfide, for example, of gold, silver, platinum or palladium, or appropriate ions thereof. Iron may actually act as either electrode depending on the identity of the other electrode. As used in the present specification and claims, the term "effective amount" refers to the amount of one electrode component which is sufficient to generate a measurable potential on the skin when combined with an effective amount of a properly selected opposite electrode component. In a typical composition, as applied on the skin, the individual electrode components are preferably present in an amount of from 0.0001–20% by weight of the formulation.

The matrix in which the components are applied can be any standard cosmetically or pharmaceutically acceptable carrier. The term "pharmaceutically or cosmetically acceptable carrier" refers to a carrier, for either pharmaceutical or cosmetic use, which carrier delivers the active components to the intended target and which will not cause harm to humans or other recipient organisms. As used herein, "pharmaceutical" or "cosmetic" will be understood to encompass both human and animal pharmaceuticals or cosmetics. The battery compositions can be prepared in any form convenient for topical application to the skin. Such forms include, but are not limited to gels, creams, dispersions, emulsions (water-in-oil or oil-in-water), suspensions, lotions, foams, mousses and the like.

The nature of the carrier can be determined in accordance with the desired method of application and/or packaging. For example, if the carrier is ionic, the carrier itself may act as an electrolyte, facilitating transfer of electrons between the two electrode components. An example of such a carrier would be any ionic cream matrix. To prevent unwanted interaction between the two "electrodes", the anode and cathode components are preferably packaged separately, either in a single, divided container made of a nonconductive material, or in entirely separate containers provided together in a single unit package. In one such embodiment, the divided container is equipped with a pump which is capable of extruding both components separately, but simultaneously. When the product is to be used, a small quantity (e.g., about 1–2 ml) of each of the components is rubbed, simultaneously or substantially simultaneously, i.e., within minutes, on the skin to be treated, and allowed to remain on the skin. In this case, the components are considered to be applied separately, in individual carriers, although application of the individual components will be simultaneous or substantially simultaneous, and the identity of the carrier of each component may be, but is not necessarily, the same. The "battery" components will then interact, resulting in electron exchange, generating an electrical current on the treated skin.

On the other hand, if a non-ionic, non-conductive matrix, for example a water-in-oil emulsion, is used, the two electrode components can be combined in the same nonconductive carrier, in a single nonconductive container, and no premature generation of current will occur. The skin itself, being conductive, can provide the necessary electrolyte function, and the single carrier containing both electrodes can be applied simultaneously and directly to the skin, thereby generating the potential once it is in contact with the skin.

Because of the skin enhancing effects of the battery compositions of the present invention, they may also have incorporated active agents which are used for skin treatment, or which are routinely applied topically. Examples of such active agents which may form part of the composition include, but are not limited to, those that improve or eradicate age spots, keratoses and wrinkles, analgesics, anesthetics, anti-acne agents, antibacterials, antiyeast agents, antifungal agents, antiviral agents, antidandruff agents, antidermatitis agents, antipruritic agents, antiemetics, antimotion sickness agents, anti-inflammatory agents, antihyperkeratolytic agents, anti-dry skin agents, antiperspirants, antipsoriatic agents, antiseborrheic agents, hair conditioners and hair treatment agents, antiaging agents, antiwrinkle agents, antiasthmatic agents and bronchodilators, sunscreen agents, antihistamine agents, skin lightening agents, depigmenting agents, wound-healing agents, vitamins, corticosteroids, tanning agents, sunscreens or hormones. More specific examples of useful active agents include retinoids, topical cardiovascular agents, clotrimazole, ketoconazole, miconozole, griseofulvin, hydroxyzine, diphenhydramine, pramoxine, lidocaine, procaine, mepivacaine, monobenzone, erythromycin, tetracycline, clindamycin, meclocyline, hydroquinone, minocycline, naproxen, ibuprofen, theophylline, cromolyn, albuterol, retinol, retinoic acid, 13-cis retinoic acid, hydrocortisone, hydrocortisone 21 acetate, hydrocortisone 17-valerate, hydrocortisone 17-butyrate, betamethasone valerate, betamethasone diproprionate, triamcinolone acetonide, fluocinonide, clobetasol, proprionate, benzoyl peroxide, crotamiton, propranolol, promethazine, vitamin A palmitate, vitamin E acetate, DHEA and derivatives thereof, alpha- or beta-hydroxy acids, and mixtures thereof. The amount of active agent to be used in any given formulation is readily determined in accordance with its usual dosage. In adding of such further components to the battery, however, consideration should be made of the redox state of the additional component, and to which electrode it is added, so that the additional component does not interfere with the intended reaction between the electrodes(e.g., by being an oxidizable component in the presence of an oxidizing electrode). The combination of the electrodes with active agents may in fact enhance the delivery of the actives, by facilitating the opening and closing of cell channels.

In a preferred embodiment, the electrode materials are incorporated into the formulation bound to an ion exchange resin, The use of the resin creates very small metal compound particles, which create greater efficiency in electron exchange. It also isolates the metal particles physically from their redox counterparts, so that there are fewer "short circuits". Ion exchange resins should be selected from those which are cosmetically or pharmaceutically compatible. In most cases, the preferred resin will be a cation exchange resin; however, when metallic complexes or polyatomic ions are used as an electrode, an anion exchange resin may be preferable, so as to provide an ionic character opposite to that of the material intended to be bound. Suitable resins are, for example, commercially available types such as Sephadex or Amberlite. The electrode compounds are bound to the resin, using standard binding techniques, before they are combined with the appropriate carrier. For ease of mixing and application, as well as aesthetics, it is preferred that the resin be in the form of beads of approximately 1–100 $\mu$ in diameter. This size is also advantageous in that each individual bead constitutes an electrode and is of the order of the size of the skin cells, thus promoting most efficient use of the resulting current at the biochemical level. In addition to ion exchange resins, polymers that bind cations, e.g., Carbopol, PVP, polyacrylic acid, or gelatin, can also be to bind the electrodes.

The battery composition, or the individual electrode components thereof, are prepared by routine mixing methods known to those skilled in the formulation arts. If a resin bead is to be used, a salt of the selected metal is added to the selected resin to form a slurry, and then contacted with an appropriate base to generate the desired metal-containing species. The electrode is then simply mixed into the chosen carrier, and packaged appropriately. Alternately, the metal hydroxide can be taken up directly by any suitable means known in the art.

The formulation also can comprise other components which may be chosen depending on the carrier and/or the intended use of the formulation. Additional components include, but are not limited to, water soluble colorants (such as FD&C Blue #1); oil soluble colorants (such as D&C Green #6); water soluble sunscreens (such as Eusolex 232); oil soluble sunscreens (such as Octyl Methoxycinnamate); particulate sunscreens (such as Zinc Oxide); antioxidants (such as BHT); chelating agents (such as Disodium EDTA); emulsion stabilizers (such as carbomer); preservatives (such as Methyl Paraben); fragrances (such as pinene); flavoring agents (such as sorbitol); humectants (such as glycerine); waterproofing agents (such as PVP/Eicosene Copolymer); water soluble film-formers (such as Hydroxypropyl methylcellulose); oil-soluble film formers (such as Hydrogenated C-9 Resin); cationic polymers (such as Polyquaternium 10); anionic polymers (such as xanthan gum); vitamins (such as Tocopherol); and the like.

The present compositions can be used in a number of different therapeutic or preventive applications. In general terms, since the presence of an electric potential at the skin surface is shown to be characteristic of normal, healthy skin, application of the battery can be employed as a regularly applied preventive of skin damage, e.g. redness and irritation commonly associated with dry skin or exposure to sun, heat and/or cold, and to promote and maintain overall skin health. It can also serve as a spot treatment to reduce the effects of inflammation or irritation on an already damaged skin surface, wherein the composition is applied, and repeated, as needed. As noted above, in this regard, the battery composition(s) may be directly mixed with other skin-active agents for use in treatment of skin conditions. However, the battery can also be used separately in the reduction of the effects of irritation and inflammation associated with dry skin, severe dry skin, dandruff, acne, keratoses, psoriasis, eczema, skin flakiness, pruritus, lentigines, melasmas, warts, blemished skin, hyperpigmented skin, hyperkeratotic skin, or inflammatory dermatoses, which conditions may or may not also be treated with a skin active agent.

In addition, the battery can be used as an adjunct to the wound healing process. As shown above, healing skin is known to be associated with a measurable, increased current. The skin battery of the present invention can be used to enhance the naturally occurring process, either by direct combination with wound-healing active agents, or alone in a separate application.

In certain embodiments, the battery may be useful as an antioxidant. For example, certain of the metals used as electrodes in the battery, such as $Fe^{+2}$, can act as antioxidants. The benefit of antioxidants, or free-radical scavengers, in promoting healthy skin is widely recognized. Thus, in such embodiments, the battery provides this additional advantage. In this regard, it is particularly useful in combination with sunscreen or suntanning formulations, where risk of skin damage due to generation of free radicals by sun exposure is high. In addition, however, regardless of any antioxidant properties, the battery can be used in sunscreen and suntanning formulations to assist in preventing and/or treating the erythema which is commonly associated with sun exposure. Similarly, the battery can be used as an after-sun treatment for the same purpose, i.e., to reduce the effects of sun-induced erythema.

It will be understood by those skilled in the art that the phrase "treatment or prevention of skin damage" as used in the present specification and claims encompasses each of the enumerated specific applications, as well as any not specifically enumerated expressly herein. In particular, it will be understood that "prevention of skin damage" is meant to include routine maintenance of skin health without reference to prevention of a specific skin condition, as well as referring to prevention of specific conditions or problems.

The invention is further illustrated in the following non-limiting examples.

EXAMPLES

Example 1

Two electrodes are prepared as follows. Into 700 g of $H_2O$ is added 0.11 g of $NaAuCl_4.2H_2O$, and 10 g Sephadex SP-C50. The components are blended to form a slurry. To the slurry is added 500 g of a 5% $NaCO_3$ solution, thereby resulting in $Au(OH)_3$ bound to the Sephadex bead.

Similarly, to form the second electrode, to 500 g $H_2O$ is added 5 g $FeCl_2.4H_2O$. This mixture is filtered to remove resulting debris, and after filtration, is blended with 10 g Sephadex SP-C50 to form a slurry. The slurry is then added to 500 g 5% NaOH solution. The resulting product is again filtered, then washed and filtered several times to remove any residual hydroxide. The resulting electrode is $Fe(OH)_2$ bound to Sephadex beads.

Example 2

The electrodes described above are incorporated separately into several different carriers, specifically a standard water-in-oil emulsion, an oil-in-water emulsion, a water-in-silicone emulsion and a gel. Each product is then tested for its ability to generate a current when applied on the skin. The base carrier, without added electrode components, is used as a control.

The control and the test sample are each applied in an area approximately one inch in diameter on the arm, approximately three to four inches apart. Electrodes of simple voltmeter(Micronta) are contacted with the test spots on the arm and the current generated at each spot is measured. In each case, the control spots yields no measurable. However, in each "battery" spot, a current of in the range of approximately 50–200 mV is observed, the level of current generated being dose-dependent. When the electrodes are cleaned and exchanged, a potential of substantially the same magnitude but opposite polarity is also observed, Thus, it is demonstrated that the compositions of the present invention can in fact generate a current when applied to the skin.

What we claim is:

1. A method for preventing or treating skin damage which comprises applying to the skin a cosmetic or pharmaceutical composition containing an effective amount of a cosmetically or pharmaceutically acceptable compound capable of acting as an electron donor, simultaneously or substantially simultaneously with the application to the same skin of a composition containing an effective amount of a cosmetically or pharmaceutically acceptable compound capable of acting as an electron acceptor, whereby an exchange of electrons between the electron donor and electron acceptor results in generation of an electrical current on the skin in the absence of an external source of electricity.

2. The method of claim 1 in which the donor and acceptor are each contained in a cosmetically or pharmaceutically acceptable carrier.

3. The method of claim 2 in which the carrier is an ionic carrier.

4. The method of claim 3 in which the donor and acceptor are applied separately in individual carriers which may be the same or different.

5. The method of claim 2 in which the carrier is a non-ionic carrier.

6. The method of claim 5 in which the donor and acceptor are applied together in the same carrier.

7. The method of claim 1 in which $Au(OH)_3$ is used as the electron acceptor.

8. The method of claim 1 in which $Fe(OH)_2$ is the electron donor.

9. The method of claim 1 in which both electron donor and electron acceptor are bound to ion exchange resin.

10. The method of claim 9 in which the resin is a cation exchange resin.

11. The method of claim 1 in which the effective amount of each of the donor and acceptor is about 0.0001–20% by weight of the total composition in which it is contained.

12. A composition containing effective amounts of a cosmetically or pharmaceutically acceptable compound capable of acting as an electron donor and a cosmetically or pharmaceutically acceptable compound capable of acting as an electron acceptor, in combination with a cosmetically or pharmaceutically acceptable carrier.

13. The composition of claim 12 in which the carrier is a non-ionic carrier.

14. The composition of claim 12 which contains an effective amount of $Au(OH)_3$.

15. The composition of claim 12 which contains an effective amount of $Fe(OH)_2$.

16. The composition of claim 12 which contains effective amounts of both $Au(OH)_3$ and $Fe(OH)_2$.

17. The composition of claim 12 in which the amount of donor and acceptor is each about 0.0001–20%.

18. The composition of claim 12 in which the donor and acceptor are each bound to an ion exchange resin.

19. The composition of claim 18 in which the resin a cation exchange resin.

20. A unit package comprising at least one composition containing an effective amount of a cosmetically or pharmaceutically acceptable compound capable of acting as an electron donor and/or a cosmetically or pharmaceutically acceptable compound capable of acting as an electron acceptor, in combination with a cosmetically or pharmaceutically acceptable carrier.

21. The package of claim 20 in which the donor and acceptor are contained in separate compositions in separate compartments within the package.

22. The package of claim 20 in which the donor and acceptor are contained in a single composition in a single compartment within the package.

23. The package of claim 20 in which the material from which the package is made is nonconductive.

24. A method for generating an electric current on the skin which comprises applying to the skin a cosmetic or pharmaceutical composition containing an effective amount of a cosmetically or pharmaceutically acceptable compound capable of acting as an electron donor, simultaneously or substantially simultaneously with the application to the same skin of a composition containing an effective amount of a cosmetically or pharmaceutically acceptable compound capable of acting as an electron acceptor, in the absence of an external source of electricity.

* * * * *